United States Patent
Osawa

(10) Patent No.: US 10,980,493 B2
(45) Date of Patent: Apr. 20, 2021

(54) MEDICAL IMAGE DISPLAY DEVICE, METHOD, AND PROGRAM

(71) Applicant: FUJIFILM Corporation, Tokyo (JP)

(72) Inventor: Akira Osawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 303 days.

(21) Appl. No.: 15/943,002

(22) Filed: Apr. 2, 2018

(65) Prior Publication Data

US 2018/0289336 A1 Oct. 11, 2018

(30) Foreign Application Priority Data

Apr. 10, 2017 (JP) .............................. JP2017-077361

(51) Int. Cl.
*A61B 5/00* (2006.01)
*G06T 19/00* (2011.01)
(Continued)

(52) U.S. Cl.
CPC ................ *A61B 5/748* (2013.01); *A61B 8/08* (2013.01); *G06K 9/6273* (2013.01); *G06T 7/0012* (2013.01); *G06T 7/0016* (2013.01); *G06T 11/00* (2013.01); *G06T 15/08* (2013.01); *G06T 19/00* (2013.01); *A61B 5/7425* (2013.01); *A61B 8/483* (2013.01); *G06T 7/11* (2017.01); *G06T 2200/24* (2013.01); *G06T 2207/10072* (2013.01);
(Continued)

(58) Field of Classification Search
CPC ......... A61B 5/748; A61B 8/08; G06K 9/6273
See application file for complete search history.

(56) References Cited

U.S. PATENT DOCUMENTS

2009/0080734 A1  3/2009  Moriya et al.
2010/0091035 A1  4/2010  Kirchberg et al.
(Continued)

FOREIGN PATENT DOCUMENTS

JP    2004-46594 A    2/2004
JP    3577680 B2     10/2004
(Continued)

OTHER PUBLICATIONS

Iwasawa, "Quantitative evaluation of CT images of interstitial pneumonia using computer," Tomographic Image Study Magazine, vol. 41 No. 2, Aug. 2014, 11 pages.
(Continued)

*Primary Examiner* — Santiago Garcia
(74) *Attorney, Agent, or Firm* — Birch, Stewart, Kolasch & Birch, LLP

(57) ABSTRACT

A classification unit classifies a lung region, which is included in each of two three-dimensional images having different imaging times for the same subject, into a plurality of types of case regions. A mapping image generation unit generates a plurality of mapping images corresponding to the three-dimensional images by labeling each of the classified case regions. A change calculation unit calculates the center-of-gravity position of each case region for case regions at corresponding positions in the mapping images, and calculates the movement amount and the movement direction of the center-of-gravity position between the mapping images as a change of each case region. A display control unit displays information regarding the change on a display.

15 Claims, 9 Drawing Sheets

(51) Int. Cl.
*G06T 7/00* (2017.01)
*G06T 11/00* (2006.01)
*A61B 8/08* (2006.01)
*G06T 15/08* (2011.01)
*G06T 7/11* (2017.01)
*G06K 9/62* (2006.01)

(52) U.S. Cl.
CPC ............... *G06T 2207/20084* (2013.01); *G06T 2207/30061* (2013.01); *G06T 2210/41* (2013.01)

(56) References Cited

U.S. PATENT DOCUMENTS

| | | | |
|---|---|---|---|
| 2010/0226550 A1 | 9/2010 | Miyasa et al. | |
| 2011/0190633 A1* | 8/2011 | Kawagishi | A61B 8/08 600/443 |
| 2014/0228678 A1* | 8/2014 | Meyer | A61B 6/487 600/424 |
| 2016/0007972 A1* | 1/2016 | Nishiura | A61B 8/5269 600/437 |
| 2016/0048972 A1* | 2/2016 | Kam | G06T 7/174 382/128 |
| 2016/0125162 A1* | 5/2016 | Takata | G06F 19/321 705/2 |
| 2016/0155227 A1* | 6/2016 | Chae | G06T 11/60 382/131 |
| 2017/0046616 A1 | 2/2017 | Socher et al. | |
| 2017/0215967 A1* | 8/2017 | Spath | G06F 19/321 |
| 2018/0326149 A1* | 11/2018 | Lipschultz | A61B 6/5217 |
| 2018/0333112 A1* | 11/2018 | Weber | A61B 8/085 |
| 2018/0344161 A1* | 12/2018 | Meyer | A61B 5/0037 |
| 2019/0362497 A1* | 11/2019 | Dwivedi | G06T 7/12 |

FOREIGN PATENT DOCUMENTS

| | | |
|---|---|---|
| JP | 2007-287018 A | 11/2007 |
| JP | 2009-45121 A | 3/2009 |
| JP | 2013-198817 A | 10/2013 |
| JP | 5661453 B2 | 1/2015 |
| WO | WO 2010/082246 A1 | 7/2010 |

OTHER PUBLICATIONS

Jacob et al., "Evaluation of computer-based computer tomography stratification against outcome models in connective tissue disease-related interstitial lung disease: a patient outcome study," BMC Medicine 14:190 (2016), pp. 1-13.

Japanese Office Action for corresponding Japanese Application No. 2017-077361, dated Aug. 4, 2020, with English translation.

"Sales of a new product to which a case searching function of diffuse pulmonary disease," "SYNAPSE Case Match," Rad Fan Online, Feb. 27, 2017, URL:https://www.e—radfan.com/product:56835.

Japanese Office Action for Japanese Application No. 2017-077361, dated Jan. 19, 2021, with English translation.

Oosawa et al., "Development and Commercialization of "SYNAPSE Case Match" Content-based Image Retrieval System for Effectively Supporting the Interpretation of Physician," Medical Imaging Technology, vol. 32, No. 1, Jan. 2014, pp. 26-31, with English abstract.

* cited by examiner

MEDICAL IMAGE DISPLAY DEVICE, METHOD, AND PROGRAM

CROSS REFERENCE TO RELATED APPLICATIONS

The present application claims priority under 35 U.S.C. § 119 to Japanese Patent Application No. 2017-077361 filed on Apr. 10, 2017. The above application is hereby expressly incorporated by reference, in its entirety, into the present application.

BACKGROUND

Technical Field

The present invention relates to a medical image display device, method, and program for identifying and displaying a plurality of types of case regions included in a medical image.

Related Art

Image diagnosis using medical images obtained by capturing a radiographic image and an ultrasound image of a patient, who is a subject, has been performed. In recent years, due to advances in medical apparatuses such as computed tomography (CT) apparatuses and magnetic resonance imaging (MRI) apparatuses, high-quality three-dimensional images with high resolution are used for image diagnosis.

Incidentally, interstitial pneumonia is known as a disease of the lung. A method of analyzing CT images of a patient with interstitial pneumonia and classifying and quantifying lesions showing specific symptoms, such as honeycomb lungs, reticular shadows, and cysts contained in the CT images, has been proposed (refer to "Evaluation of computer-based computer tomography stratification against outcome models in connective tissue disease-related interstitial lung disease: a patient outcome study, Joseph Jacobl, BMC Medicine (2016) 14:190, DOI 10. 1186/s12916-016-0739-7" and "Quantitative evaluation of CT images of interstitial pneumonia using computer, Tae Iwasawa, tomographic image study Magazine Vol. 41, No. 2, August 2014"). By analyzing the CT images and classifying and quantifying lesions in this manner, the degree of lung disease can be easily determined. In addition, by assigning different colors to the regions classified and quantified in this manner, it is possible to easily determine how much a region of a specific symptom is included in the image.

On the other hand, in order to diagnose the recovery or progression of a disease, there is a case where comparative observation over time is performed using past medical images of the same patient. For example, JP3577680B has proposed a method of displaying a time-varying portion with an increased emphasis degree by calculating a difference image between radiographic images of the chest having different imaging times, labeling a portion corresponding to the time-varying portion in the difference image, and expressing a time-varying region having a predetermined size or more with a fill pattern or the like. In addition, JP5661453B has proposed a method of displaying a motion picture after performing registration between corresponding parts in CT images having different imaging times.

In order to extract a structure, such as an organ of interest, from a three-dimensional image, it is necessary to detect the structure in the three-dimensional image. In order to classify pixels of interest in an image into a plurality of classes, a method of deep learning has been proposed. Deep learning is a machine learning method using a multilayered neural network constructed by hierarchically connecting a plurality of processing layers.

In deep learning, in each layer of the multilayered neural network, arithmetic processing is performed on a plurality of different pieces of calculation result data obtained from the preceding hierarchy with respect to input data, that is, feature amount extraction result data. Then, by performing further arithmetic processing on the feature amount data obtained by the above processing in the subsequent processing layer, it is possible to improve the recognition rate of feature amounts and classify the input data into a plurality of classes.

It is conceivable to apply such a deep learning method to the three-dimensional image in order to classify the pixels of the three-dimensional image into a plurality of classes. For example, in the case of classifying a plurality of types of structures included in a three-dimensional image, deep learning is performed on the neural network with the three-dimensional image being an input so that each pixel to be processed in the three-dimensional image is classified into one of the plurality of types of structures. By using the deep-learned neural network in this manner, it is possible to classify each target pixel of the input three-dimensional image into any of the plurality of types of structures.

For the interstitial lung disease described above, it is also desired to accurately perform comparative observation over time using the result of mapping between the past image and the latest image. However, in the case of the interstitial lung disease, regions showing a plurality of symptoms are included in the lung. Accordingly, it is difficult to accurately perform the comparative observation over time by accurately displaying a region change for each symptom.

SUMMARY

The invention has been made in view of the above circumstances, and it is an object of the invention to make it possible to accurately perform comparative observation over time using images of a disease, such as an interstitial lung disease.

A first medical image display device according to the invention comprises: classification unit for classifying a target region, which is included in each of a plurality of medical images having different imaging times for the same subject, into a plurality of types of case regions; mapping image generation unit for generating a mapping image relevant to each of the case regions, which corresponds to each of the plurality of medical images, by labeling each of the case regions; change calculation unit for calculating a center-of-gravity position of a case region at each corresponding position for case regions at corresponding positions in the plurality of mapping images and calculating at least one of a movement amount or a movement direction of the center-of-gravity position between the plurality of mapping images as a change of each of the classified case regions between the plurality of mapping images; and display control unit for displaying information regarding the change on display unit.

In the first medical image display device according to the invention, the change calculation unit may further calculate, as the change, an amount of change in a size of a case region at a corresponding position in each of the plurality of mapping images.

A second medical image display device according to the invention comprises: classification unit for classifying a target region, which is included in each of a plurality of medical images having different imaging times for the same subject, into a plurality of types of case regions; mapping image generation unit for generating a plurality of mapping images corresponding to the plurality of medical images by labeling each of the case regions; change calculation unit for calculating an amount of change in a size of a case region at each corresponding position in the plurality of mapping images as a change of each of the classified case regions between the plurality of mapping images; and display control unit for displaying information regarding the change on display unit.

The "case region" means a region showing a specific symptom or specific form within the target region. Therefore, in the invention, it is assumed that a region of a structure itself showing a specific form, such as the heart and the diaphragm, is also included in the case region.

The first and second medical image display devices according to the invention may further comprise registration unit for performing registration between the plurality of medical images and performing registration between the plurality of mapping images based on the registration result.

In this case, the registration unit may perform designated registration among first registration for aligning a position of a medical image other than a medical image having an oldest imaging time, among the plurality of medical images, with the oldest medical image, second registration for aligning a position of a medical image other than a medical image having a latest imaging time with the latest medical image, and third registration for aligning a position of a medical image other than a designated medical image with the designated medical image.

In the first and second medical image display devices according to the invention, the classification unit may have a discriminator that is deep-learned so as to classify the plurality of types of cases, and may classify the target region into a plurality of types of case regions using the discriminator.

The first and second medical image display devices according to the invention may further comprise storage unit for storing information regarding a change of each of the case regions for a plurality of subjects. The display control unit may acquire information regarding a change of each of the case regions for a subject different from a subject to be displayed from the storage unit and further display the acquired information regarding the change.

The "information relevant to the change of each case region" means information indicating how each case region changes in the future. For example, the fact that a certain case region has spread and became worse or the fact that a certain case region has been narrowed and cured due to administration of medicine can be used as information regarding the change of each case region.

A first medical image display method according to the invention comprises: classifying a target region, which is included in each of a plurality of medical images having different imaging times for the same subject, into a plurality of types of case regions; generating a mapping image relevant to each of the case regions, which corresponds to each of the plurality of medical images, by labeling each of the case regions; calculating a center-of-gravity position of a case region at each corresponding position for case regions at corresponding positions in the plurality of mapping images and calculating at least one of a movement amount or a movement direction of the center-of-gravity position between the plurality of mapping images as a change of each of the classified case regions between the plurality of mapping images; and displaying information regarding the change on display unit.

A second medical image display method according to the invention comprises: classifying a target region, which is included in each of a plurality of medical images having different imaging times for the same subject, into a plurality of types of case regions; generating a plurality of mapping images corresponding to the plurality of medical images by labeling each of the case regions; calculating an amount of change in a size of a case region at each corresponding position in the plurality of mapping images as a change of each of the classified case regions between the plurality of mapping images; and displaying information regarding the change on display unit.

In addition, a program causing a computer to execute the first and second medical image display methods according to the present invention may be provided.

Another first medical image display device according to the invention comprises: a memory that stores commands to be executed by a computer; and a processor configured to execute the stored commands. The processor executes: processing for classifying a target region, which is included in each of a plurality of medical images having different imaging times for the same subject, into a plurality of types of case regions; processing for generating a mapping image relevant to each of the case regions, which corresponds to each of the plurality of medical images, by labeling each of the case regions; processing for calculating a center-of-gravity position of a case region at each corresponding position for case regions at corresponding positions in the plurality of mapping images and calculating at least one of a movement amount or a movement direction of the center-of-gravity position between the plurality of mapping images as a change of each of the classified case regions between the plurality of mapping images; and processing for displaying information regarding the change on display unit.

Another second medical image display device according to the invention comprises: a memory that stores commands to be executed by a computer; and a processor configured to execute the stored commands. The processor executes: processing for classifying a target region, which is included in each of a plurality of medical images having different imaging times for the same subject, into a plurality of types of case regions; processing for generating a plurality of mapping images corresponding to the plurality of medical images by labeling each of the case regions; processing for calculating an amount of change in a size of a case region at each corresponding position in the plurality of mapping images as a change of each of the classified case regions between the plurality of mapping images; and processing for displaying information regarding the change on display unit.

According to the first medical image display device and method of the invention, a target region included in each of the plurality of medical images having different imaging times for the same subject is classified into a plurality of types of case regions, and a mapping image relevant to each of the case regions corresponding to each of the plurality of medical images is generated by labeling each of the case regions. The center-of-gravity position of a case region is calculated for case regions at corresponding positions in the plurality of mapping images, at least one of the movement amount or the movement direction of the center-of-gravity position between the plurality of mapping images is calculated as a change of each classified case region between the plurality of mapping images, and information regarding the change is displayed on the display unit. As described above, in the invention, since at least one of the movement amount or the movement direction of the center-of-gravity position of each case region at the corresponding position between the plurality of mapping images is calculated as changes of each case region, it is possible to accurately calculate the change of the case region. Therefore, it is possible to accurately perform comparative observation over time using a plurality of medical images having different imaging times.

According to the second medical image display device and method of the invention, a target region included in each of the plurality of medical images having different imaging times for the same subject is classified into a plurality of types of case regions, and a mapping image relevant to each of the case regions corresponding to each of the plurality of medical images is generated by labeling each of the case regions. The amount of change in the size of a case region at each corresponding position in the plurality of mapping images is calculated as a change of each classified case region between the plurality of mapping images, and information regarding the change is displayed on the display unit. As described above, in the invention, since the amount of change in the size of the case region at each corresponding position is calculated as a change of each case region, it is possible to accurately calculate the change of the case region. Therefore, it is possible to accurately perform comparative observation over time using a plurality of medical images having different imaging times.

DETAILED DESCRIPTION

Figure 1:
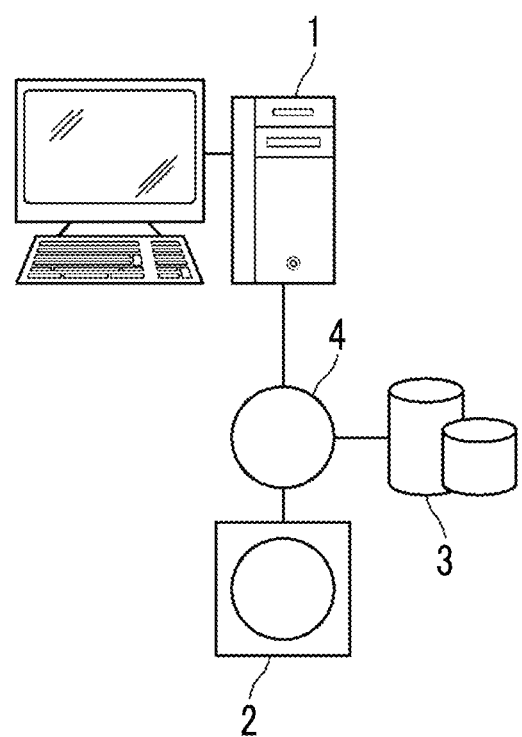
FIG. 1 is a hardware configuration diagram showing an outline of a diagnostic support system to which a medical image display device according to an embodiment of the invention is applied.

Hereinafter, an embodiment of the invention will be described with reference to the accompanying diagrams. FIG. 1 is a hardware configuration diagram showing the outline of a diagnostic support system to which a medical image display device according to an embodiment of the invention is applied. As shown in FIG. 1, in the diagnostic support system, a medical image display device 1 according to the present embodiment, a three-dimensional image cap-turing apparatus 2, and an image storage server 3 are communicably connected to each other through a network 4.

The three-dimensional image capturing apparatus 2 is an apparatus that generates a three-dimensional image showing a part, which is a part to be examined of a subject, by imaging the part. Specifically, the three-dimensional image capturing apparatus 2 is a CT apparatus, an MRI apparatus, a positron emission tomography (PET) apparatus, or the like. The three-dimensional image generated by the three-dimensional image capturing apparatus 2 is transmitted to the image storage server 3 and is stored therein. In the present embodiment, the diagnostic target part of the patient who is a subject is the lungs, and the three-dimensional image capturing apparatus 2 is a CT apparatus and generates a CT image of the chest including the lungs of the subject as a three-dimensional image V0.

The image storage server 3 is a computer that stores and manages various kinds of data, and includes a large-capacity external storage device and software for database management. The image storage server 3 communicates with other devices through the wired or wireless network 4 to transmit and receive image data or the like. Specifically, the image storage server 3 acquires various kinds of data including the image data of the three-dimensional image V0 generated by the three-dimensional image capturing apparatus 2 through the network, and stores the various kinds of data in a recording medium, such as a large-capacity external storage device, and manages the various kinds of data. The storage format of image data and the communication between devices through the network 4 are based on a protocol, such as a digital imaging and communication in medicine (DI-COM). In the present embodiment, it is assumed that a plurality of three-dimensional images having different imaging times for the same subject are stored in the image storage server 3.

The medical image display device 1 is realized by installing a medical image display program of the invention on one computer. The computer may be a workstation or a personal computer that is directly operated by a doctor who performs diagnosis, or may be a server computer connected to these through a network. The medical image display program is distributed by being recorded on a recording medium, such as a digital versatile disc (DVD) or a compact disk read only memory (CD-ROM), and is installed onto the computer from the recording medium. Alternatively, the medical image display program and the learning program are stored in a storage device of a server computer connected to the network or in a network storage so as to be accessible from the outside, and are downloaded and installed onto a computer used by a doctor as necessary.

Figure 2:
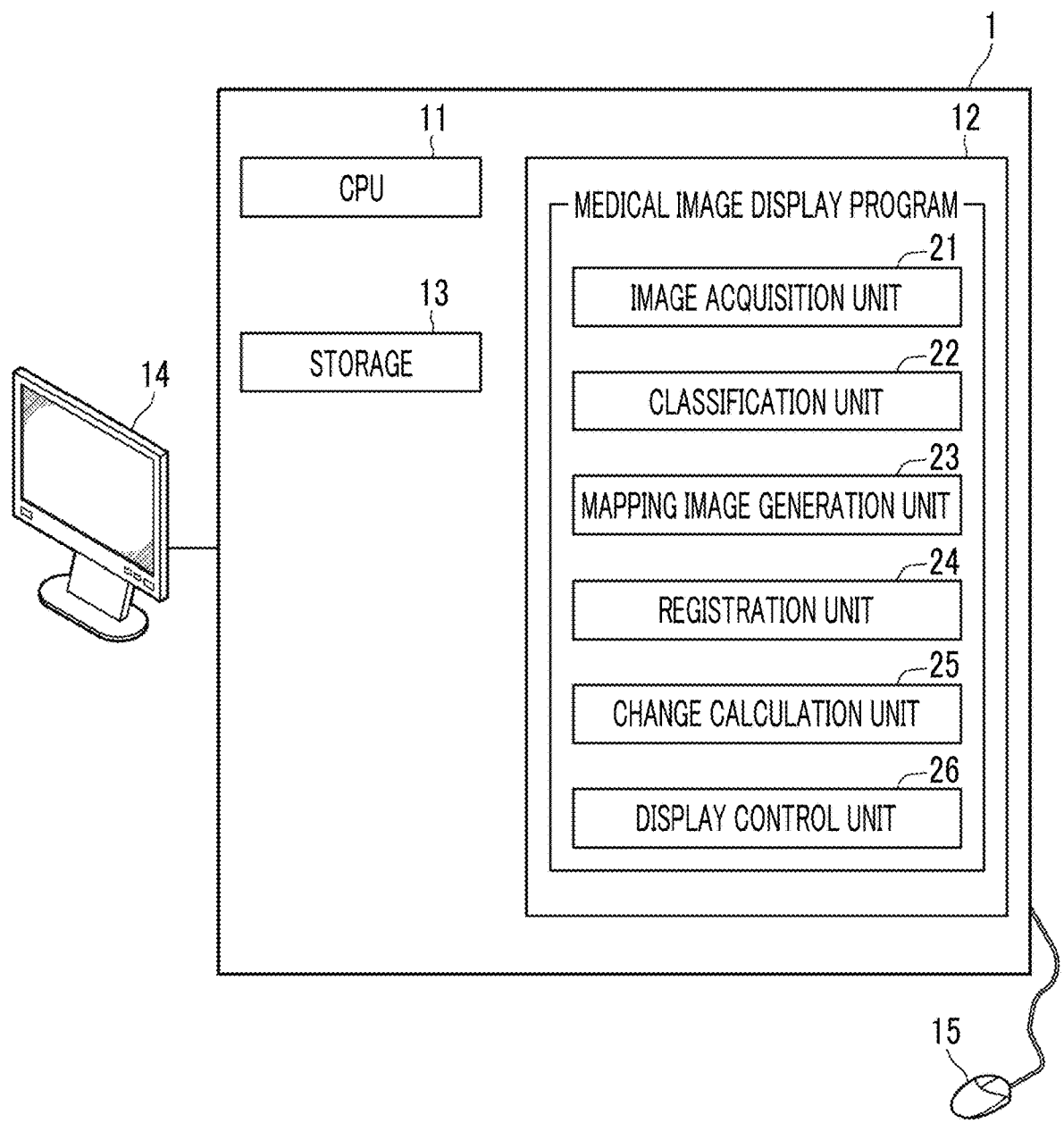
FIG. 2 is a schematic block diagram showing the configuration of the medical image display device according to the present embodiment.

FIG. 2 is a diagram showing the schematic configuration of a medical image display device realized by installing a medical image display program on a computer. As shown in FIG. 2, the medical image display device 1 includes a central processing unit (CPU) 11, a memory 12, and a storage 13 as the configuration of a standard workstation. A display 14 and an input unit 15, such as a mouse, are connected to the medical image display device 1.

Three-dimensional images of the subject acquired from the image storage server 3 through the network 4 and various kinds of information including information necessary for processing are stored in the storage 13.

A medical image display program is stored in the memory 12. As processing to be executed by the CPU 11, the medical image display program defines: image acquisition processing for acquiring a plurality of three-dimensional images having different imaging times for the same subject; classification processing for classifying a target region included in each of the plurality of three-dimensional images into a plurality of types of case regions; mapping image generation processing for generating a mapping image for each case region corresponding to each of the plurality of three-dimensional images by labeling each case region; registration processing for performing registration between the plurality of three-dimensional images and performing registration between a plurality of mapping images based on the registration result; change calculation processing for calculating a center-of-gravity position of a case region at a corresponding position in each of the plurality of mapping images and calculating at least one of a movement amount or a movement direction of the center-of-gravity position between the plurality of mapping images as a change of each classified case region between the plurality of mapping images; and display control processing for displaying information regarding the change on the display 14.

The CPU 11 executes these processes according to the program, so that the computer functions as an image acquisition unit 21, a classification unit 22, a mapping image generation unit 23, a registration unit 24, a change calculation unit 25, and a display control unit 26. The medical image display device 1 may include a plurality of processors or processing circuits for performing image acquisition processing, classification processing, mapping image generation processing, registration processing, change calculation processing, and display control processing. The medical image display device 1 of the present embodiment may be configured to include only the classification unit 22, the mapping image generation unit 23, the registration unit 24, the change calculation unit 25, and the display control unit 26. In the present embodiment, a target region is a lung region included in a three-dimensional image. The storage 13 and the image storage server 3 correspond to storage unit.

The image acquisition unit 21 acquires a plurality of three-dimensional images having different imaging times for the same subject from the image storage server 3. In a case where three-dimensional images are already stored in the storage 13, the image acquisition unit 21 may acquire the three-dimensional images from the storage 13. In the present embodiment, for the comparative observation over time, it is assumed that a latest three-dimensional image V0 and a three-dimensional image V1 having an imaging time earlier than the latest three-dimensional image V0 are acquired.

The classification unit 22 classifies a lung region included in each of the three-dimensional images V0 and V1 into a plurality of types of case regions. Since the classification processing for the three-dimensional images V0 and V1 is the same, only the classification processing for the three-dimensional image V0 will be described herein, and the explanation of the classification processing for the three-dimensional image V1 will be omitted.

In the present embodiment, the classification unit 22 has a discriminator that is a multilayered neural network deep-learned so as to be able to classify a lung region into a plurality of types of case regions. In the multilayered neural network, arithmetic processing is performed on a plurality of different pieces of calculation result data obtained from the preceding hierarchy with respect to input data, that is, feature amount extraction result data, using various kernels in each layer, feature amount data obtained as described above is acquired, and further arithmetic processing is performed on the feature amount data in the subsequent processing layer, so that it is possible to improve the recognition rate of feature amounts and classify the input data into a plurality of classes.

In the present embodiment, a multilayered neural network 40 outputs the result of the classification of the lung region into a plurality of types of case regions with the three-dimensional image V0 as an input. However, the multilayered neural network 40 can also be configured to output the result of the classification of the lung region into a plurality of types of case regions with a two-dimensional tomographic image, which shows each tomographic plane of a subject that forms the three-dimensional image V0, as an input.

Figure 3:
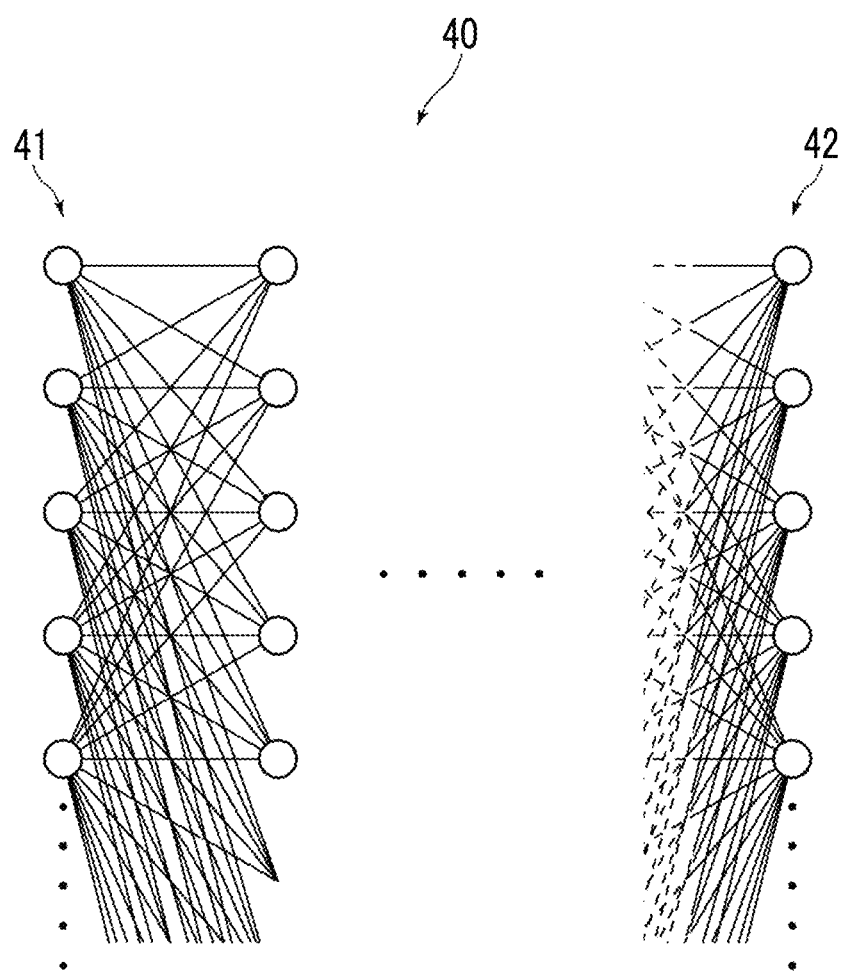
FIG. 3 is a diagram showing an example of a multilayered neural network.

FIG. 3 is a diagram showing an example of a multilayered neural network. As shown in FIG. 3, the multilayered neural network 40 has a plurality of hierarchies including an input layer 41 and an output layer 42. In the present embodiment, learning is performed such that a lung region included in the three-dimensional image V0 is classified into 33 types of case regions, that is, normal lung, ground glass opacity (GGO) tumor nodule shadow, mixed tumor nodule shadow, solid tumor nodule shadow, frosted glass shadow, pale frosted glass shadow, centrilobular frosted glass shadow, consolidation, low absorption, centrilobular emphysema, panlobular emphysema, normal pulmonary emphysema tendency, cyst, tree-in-bud appearance (TIB), small nodule (non-lobular centrality), centrilobular nodule shadow, interlobular septum thickening, bronchial wall thickening, bronchodilation, dilation of small bronchus, bronchogram, traction bronchodilation, cavitary infiltration shadow, cavitary tumor, reticular shadow, fine reticular shadow, honeycomb lung, pleural effusion, pleural thickening, chest wall, heart, diaphragm, and blood vessel. In the present embodiment, the case region includes a region showing a specific symptom or specific form within the lung region. Therefore, in the present embodiment, it is assumed that a region of a structure itself showing a specific form, such as the heart and the diaphragm, is also included in the case region.

In the present embodiment, the multilayered neural network 40 is made to learn 33 types of cases using a large number of teacher data (millions of pieces of teacher data). During learning, a voxel region normalized to a predetermined size (for example, 1.5 cm×1.5 cm×1.5 cm) is cut out from a three-dimensional image having a known case, and the image of the cut voxel region is used as teacher data. Then, the teacher data is input to the multilayered neural network 40, and the multilayered neural network 40 outputs a case region classification result. Then, the output result is compared with the teacher data, and the weight of coupling between hierarchies of units (indicated by circles in FIG. 3) included in respective layers of the multilayered neural network 40 is modified from the output side to the input side according to whether or not the output result is a correct solution or an incorrect solution. The modification of the weight of coupling is repeated a predetermined number of times or until the accuracy rate of the output classification result becomes 100% using a large number of teacher data, and the learning is ended.

For classification, the classification unit 22 extracts a lung region, which is a target region, from the three-dimensional image V0. As a method of extracting a lung region, it is possible to use any method, such as a method in which the signal value of each pixel in the three-dimensional image V0 is expressed using a histogram and threshold processing is performed to extract the lung or a region growing method based on a seed point showing the lung.

The classification unit 22 sequentially cuts out the same region as the teacher data from the extracted lung region, and inputs the cut region to a discriminator that is the multilayered neural network 40 learned as described above.

As a result, for a central pixel of the cut region, values indicating classification results for 33 types of case regions are output. The multilayered neural network 40 classifies the central pixel of the input region into a case region having the largest value among the 33 outputs of the multilayered neural network 40. As a result, all the pixels of the lung region included in the three-dimensional image V0 are classified into 33 types of case regions.

The mapping image generation unit 23 generates a plurality of mapping images M0 and M1 relevant to each case region corresponding to the three-dimensional images V0 and V1, respectively, by labeling each case region classified by the classification unit 22. The generation of a mapping image will be described only for the three-dimensional image V0, and the generation of a mapping image for the three-dimensional image V1 will be omitted.

Figure 4:
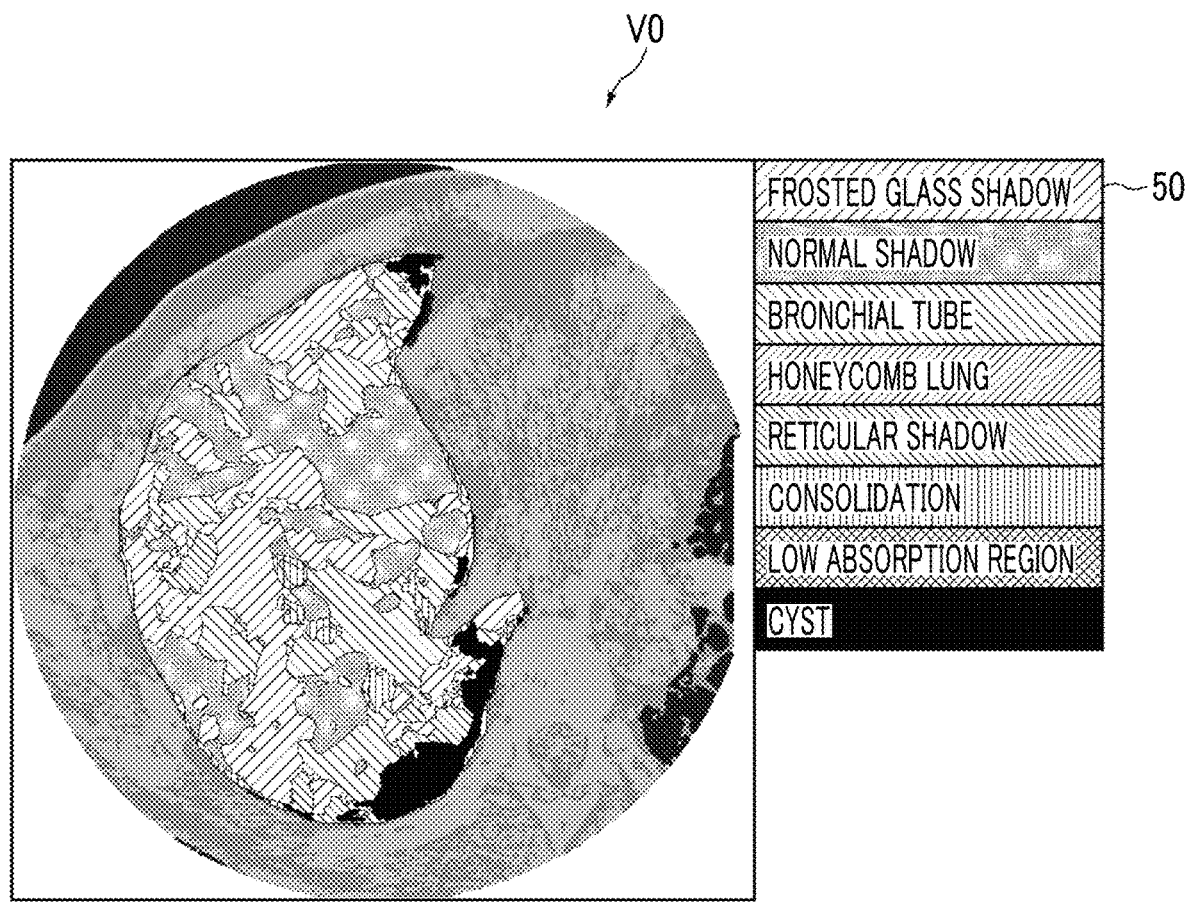
FIG. 4 is a diagram showing a three-dimensional image in which colors corresponding to classifications are assigned.

In order to make the displayed mapping image M0 easier to see, the mapping image generation unit 23 groups the 33 types of case regions classified by the classification unit 22 into eight types of case regions. Then, the mapping image generation unit 23 extracts pixels classified into the same class for each pixel of the lung region included in the three-dimensional image V0. The mapping image generation unit 23 assigns the same color to pixels extracted in each of the classifications of the eight types of case regions. FIG. 4 is a diagram showing a three-dimensional image in which colors corresponding to case regions are assigned. In FIG. 4, a tomographic image of a certain tomographic plane in the three-dimensional image V0 is shown, but V0 is shown as a reference numeral. As shown in FIG. 4, 33 types of case regions are grouped into eight types of case regions of frosted glass shadow, normal shadow, bronchial tube, honeycomb lung, reticular shadow, consolidation, low absorption region, and cyst, and different colors are assigned to these. In FIG. 4, the fact that the colors are different is shown by different patterns. In addition, FIG. 4 shows a reference 50 indicating which case each color is.

The mapping image generation unit 23 generates the three-dimensional mapping image M0 corresponding to the three-dimensional image V0 by labeling a case region having a predetermined volume or more for case regions classified into eight types. In a case where the mapping image M0 is a tomographic image, the labeling is performed for a case region having a predetermined area or more.

Figure 5:
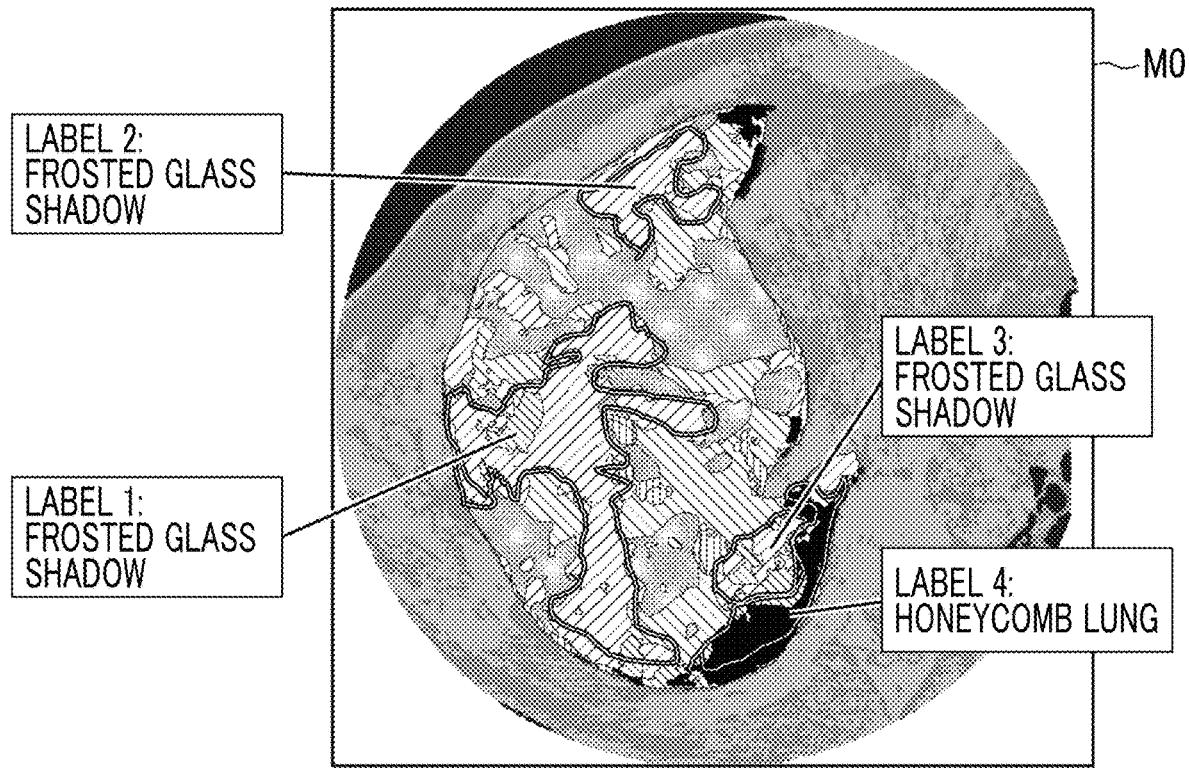
FIG. 5 is a diagram showing a mapping image.

FIG. 5 is a diagram showing a mapping image. FIG. 5 shows a mapping image for the tomographic image shown in FIG. 4. In FIG. 5, in order to simplify the explanation, labeling is performed only for case regions classified as frosted glass shadow and honeycomb lung. As shown in FIG. 5, in the mapping image M0, labeling of labels 1 to 3 is performed for three regions classified as the frosted glass shadow, and labeling of label 4 is performed for one region classified as the honeycomb lung.

The registration unit 24 performs registration between the three-dimensional images V0 and V1, and performs registration between the plurality of mapping images M0 and M1 based on the registration result. Here, the three-dimensional images V0 and V1 are acquired by imaging the chest of the same subject. However, due to breathing, posture change, and changes in imaging conditions such as an imaging range, the position, shape, size, and the like of the included structure change. Therefore, the registration unit 24 performs registration between the three-dimensional image V0 and the three-dimensional image V1. In the present embodiment, the position of the latest three-dimensional image V0 is aligned with the three-dimensional image V1 with the three-dimensional image V1 having an old imaging time as a reference. However, the position of the three-dimensional image V1 having an old imaging time may be aligned with the three-dimensional image V0 with the latest three-dimensional image V0 as a reference. An image serving as a reference for registration may be set in advance, or may be determined according to an operator's instruction from the input unit 15. Alternatively, registration between the three-dimensional images V0 and V1 may be performed with a three-dimensional image different from the three-dimensional images V0 and V1 as a reference. In this case, the reference three-dimensional image may be determined by the operator's input from the input unit 15.

For corresponding pixels of the three-dimensional image V0 and the three-dimensional image V1, the registration unit 24 calculates the shift amount and direction of each pixel of the three-dimensional image V0 with respect to the corresponding pixel of the three-dimensional image V1. Then, based on the calculated shift amount and direction, the three-dimensional image V0 is non-linearly transformed for registration of the three-dimensional image V0 with respect to the three-dimensional image V1. The registration method is not limited thereto, and any other method can be used. For example, it is possible to use a method disclosed in JP2002-032735A in which registration is performed in a local region after rough registration between two images is performed.

The registration unit 24 performs registration between the mapping images M0 and M1 based on the registration result between the three-dimensional image V0 and the three-dimensional image V1. Specifically, based on the calculated shift amount and direction, the mapping image M0 is non-linearly transformed for registration of the mapping image M0 with respect to the mapping image M1.

In the present embodiment, the classification processing and the mapping image generation processing may be performed after performing registration between the three-dimensional images V0 and V1 first.

The change calculation unit 25 calculates the center-of-gravity position of each case region for case regions at corresponding positions in the plurality of mapping images M0 and M1, and calculates at least one of the movement amount or the movement direction of the center-of-gravity position between the plurality of mapping images M0 and M1 as a change of each classified case region between the plurality of mapping images M0 and M1. In the present embodiment, it is assumed that both the movement amount and the movement direction of the center-of-gravity position are calculated. Therefore, the change calculation unit 25 calculates the center-of-gravity position of a labeled case region in each of the mapping images M0 and M1.

Figure 6:
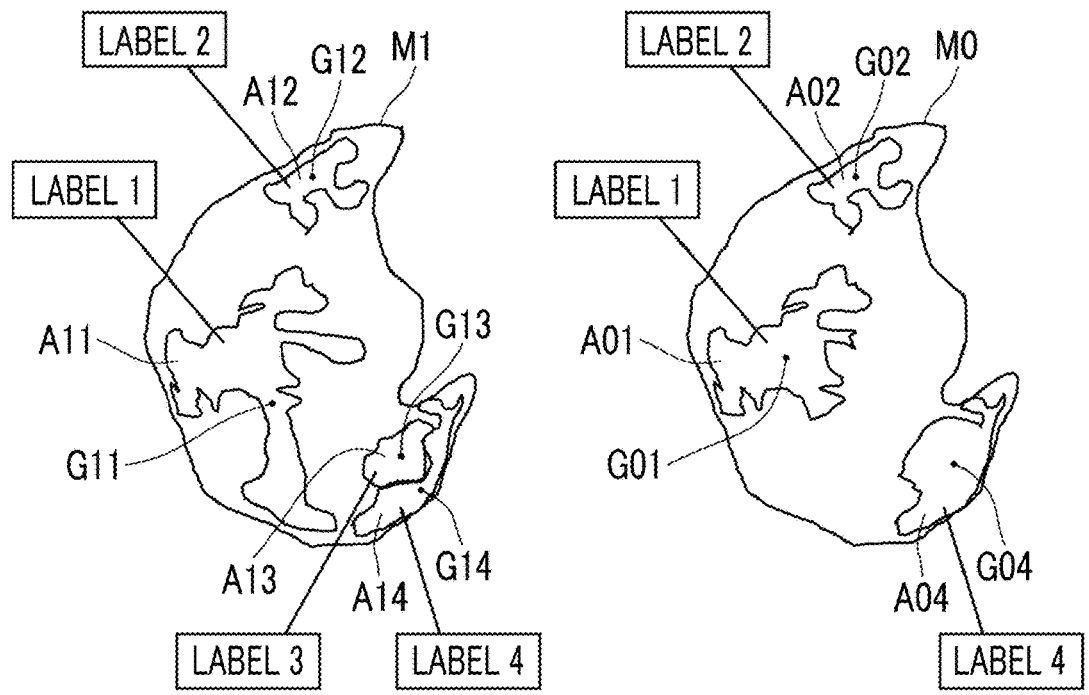
FIG. 6 is a diagram illustrating the calculation of a center-of-gravity position.

FIG. 6 is a diagram illustrating the calculation of the center-of-gravity position. In FIG. 6, the mapping images M0 and M1 of one tomographic plane included in the three-dimensional images V0 and V1 are shown. In FIG. 6, four case regions A11 to A14 corresponding to labels 1 to 4 shown in FIG. 5 are shown in the mapping image M1. In the mapping image M0, since the case region A13 in the mapping image M1 worsens to become the honeycomb lung, the case region A13 is classified so as to be integrated with the case region A14. Therefore, in the mapping image M0, three case regions A01, A02, and A04 are shown. As shown in FIG. 6, in the mapping image M1, center-of-gravity positions G11 to G14 in the case regions A11 to A14 are calculated, and in the mapping image M0, center-of-gravity positions G01, G02, and G04 in the case regions A01, A02, and A04 are calculated.

Figure 7:
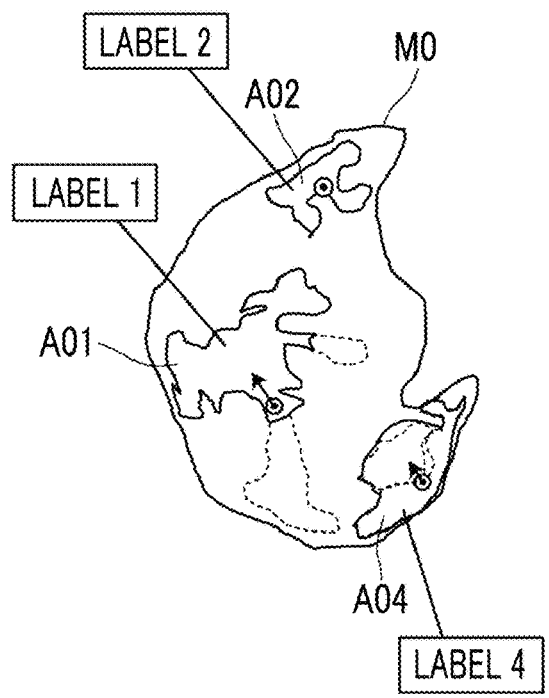
FIG. 7 is a diagram showing the movement amount and the movement direction of the center-of-gravity position.

The change calculation unit 25 calculates the movement amount and the movement direction of the center-of-gravity position for corresponding case regions in the mapping image M1 and the mapping image M0. FIG. 7 is a diagram showing the movement amount and the movement direction of the center-of-gravity position. In the mapping image M1 and the mapping image M0, the case region A11 and the case region A01 of the label 1 correspond to each other, the case region A12 and the case region A02 of the label 2 correspond to each other, and the case region A14 and the case region A04 of the label 4 correspond to each other. For the case region A11 and the case region A01 of the label 1, the movement amount and the movement direction of the center-of-gravity position G11 with respect to the center-of-gravity position G01 are calculated. For the case region A12 and the case region A02 of the label 2, the movement amount and the movement direction of the center-of-gravity position G12 with respect to the center-of-gravity position G02 are calculated. For the case region A14 and the case region A04 of the label 4, the movement amount and the movement direction of the center-of-gravity position G14 with respect to the center-of-gravity position G04 are calculated. The change calculation unit 25 assigns the calculated movement direction and movement amount of the center-of-gravity position to the mapping image M0 as a vector. In FIG. 7, vectors indicating the movement amounts and the movement directions of the center-of-gravity positions of the case regions A01, A02, and A04 in the mapping image M0 as viewed from the mapping image M1 are shown. As for the case regions A12 and A02 of the label 2, since the center-of-gravity position is not moved, no vector is shown.

Looking at the mapping image M0 to which vectors are assigned, it can be seen that, for the case region A01, the center-of-gravity position has moved since the area (volume in the case of a three-dimensional image) is smaller than that of the case region A11. For the case region A02, it can be seen that there is no change compared with the case region A12. For the case region A04, it can be seen that the center-of-gravity position has moved since the area is larger than that of the case region A14.

In the present embodiment, the change calculation unit 25 also calculates the amount of change in the size of each case region as a change. As the amount of change in size, a difference value between the area (volume in the case of a three-dimensional image) of the case region A01 and the area of the case region A11, a difference value between the area of the case region A02 and the area of the case region A12, and a difference value between the area of the case region A04 and the area of the case region A14 may be calculated. In addition, the change rate of the area of the case region A01 from the area of the case region A11, the change rate of the area of the case region A02 from the area of the case region A12, and the change rate of the area of the case region A04 from the area of the case region A14 may be calculated.

Figure 8:
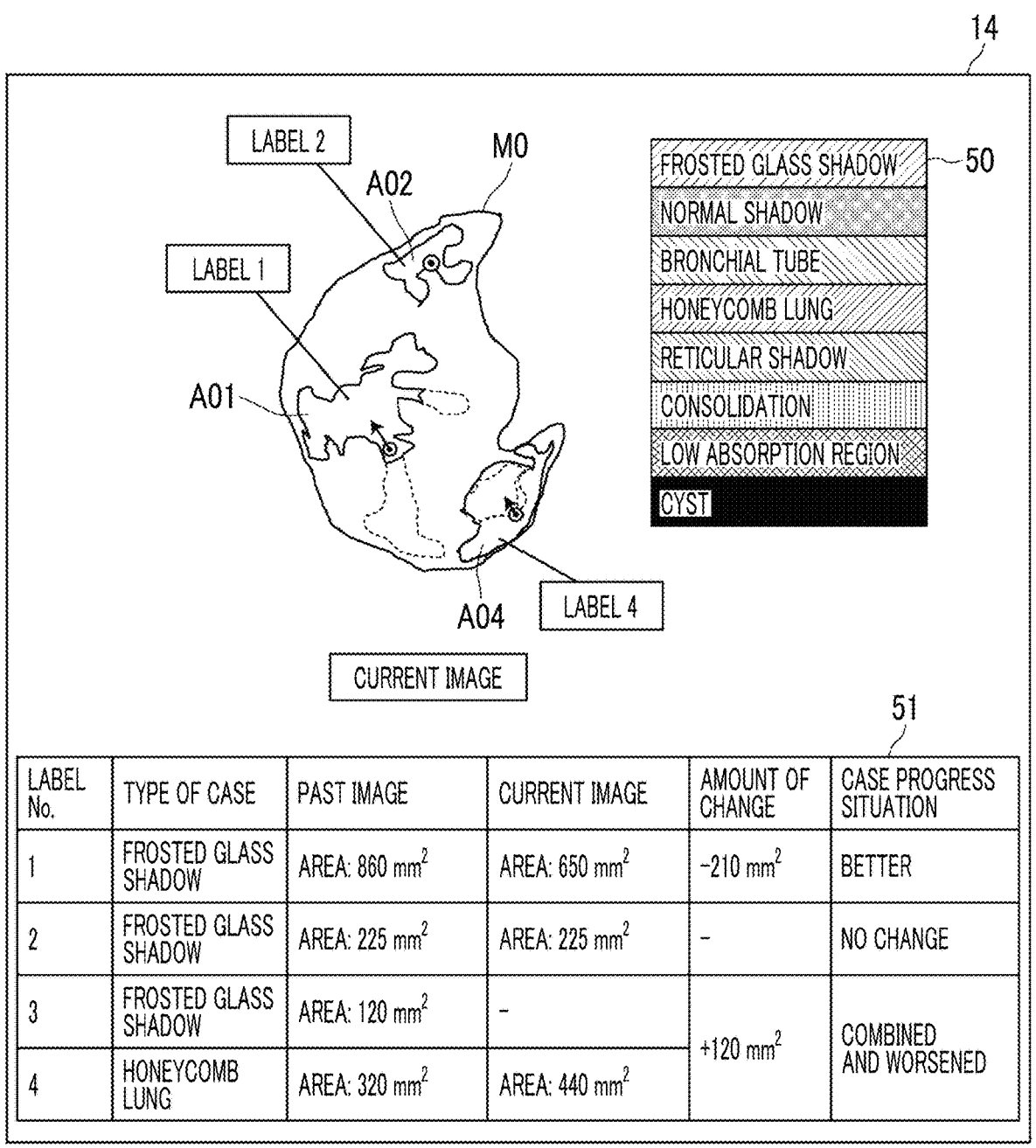
FIG. 8 is a diagram showing information regarding a displayed change.

The display control unit 26 displays information regarding the change calculated by the change calculation unit 25 on the display 14. FIG. 8 is a diagram showing information regarding the displayed change. As shown in FIG. 8, the same mapping image M0 as in FIG. 7 and a table 51 showing information regarding the change are displayed on the display 14. The reference shown in FIG. 4 is shown next to the mapping image M0. In FIG. 8, only the frosted glass shadow and the honeycomb lung are shown in the mapping image M0 for ease of explanation. In practice, however, labeling results for the eight classifications are shown. Similarly to FIG. 7, vectors indicating the movement amounts and the movement directions of the center-of-gravity positions of the case regions A01, A02, and A04 in the mapping image M0 as viewed from the mapping image M1 are shown. The table 51 shows the type of a case, the area in a past image (that is, the three-dimensional image V1), the area in a current image (that is, the three-dimensional image V0), the amount of change in area, and a case progression situation for the labels 1 to 4. In a case where the mapping image M0 is a three-dimensional image, instead of the area, the volume in a past image, the volume in a current image, and the amount of change in volume are shown in the table 51.

Figure 9:
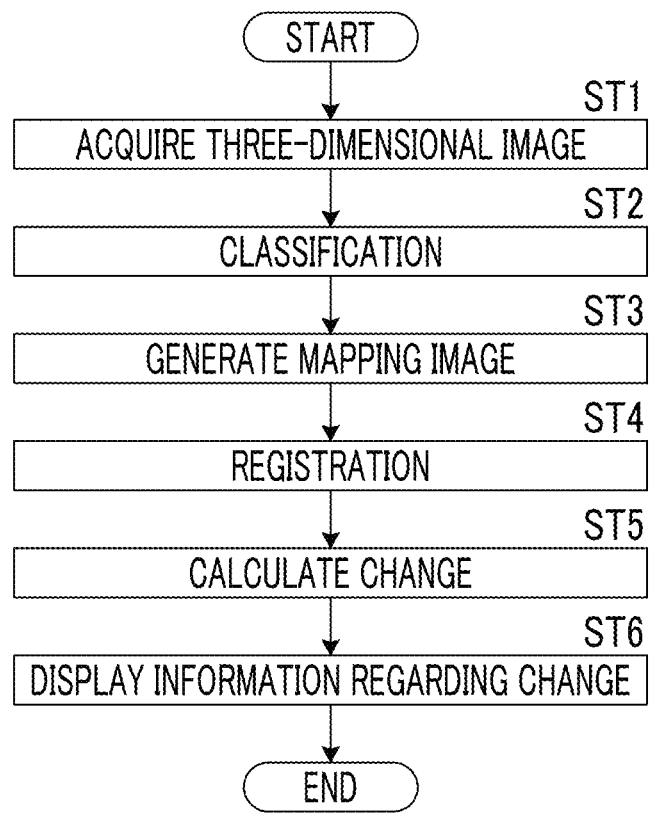
FIG. 9 is a flowchart showing a process performed in the present embodiment.

Next, a process performed in the present embodiment will be described. FIG. 9 is a flowchart showing the process performed in the present embodiment. First, the image acquisition unit 21 acquires the two three-dimensional images V0 and V1 having different imaging times for the same subject (step ST1). Then, the classification unit 22 classifies a lung region included in each of the three-dimensional images V0 and V1 into a plurality of types of case regions (step ST2). Then, the mapping image generation unit 23 generates a plurality of mapping images M0 and M1 relevant to each case region corresponding to the three-dimensional images V0 and V1, respectively, by labeling each of the classified case regions (step ST3). Then, the registration unit 24 performs registration between the three-dimensional images V0 and V1, and performs registration between the mapping images M0 and M1 based on the registration result (step ST4). The change calculation unit 25 calculates the center-of-gravity position of each case region for case regions at corresponding positions in the mapping images M0 and M1, and calculates the movement amount and the movement direction of the center-of-gravity position and the amount of change in size between the mapping images M0 and M1 as changes of each classified case region (step ST5). Then, the display control unit 26 displays information regarding the change on the display 14 (step ST6), and ends the process.

As described above, in the present embodiment, since the movement amount and the movement direction of the center-of-gravity position of each case region at the corresponding position between the plurality of mapping images M0 and M1 are calculated as changes of each case region, it is possible to accurately calculate the change of the case region. Therefore, it is possible to accurately perform comparative observation over time using a plurality of three-dimensional images V0 and V1 having different imaging times.

In addition, since the change of each case region can be more accurately calculated by performing registration between the three-dimensional images V0 and V1 and performing registration between a plurality of mapping images M0 and M1 based on the registration result, it is possible to more accurately perform the comparative observation over time using a plurality of three-dimensional images V0 and V1 having different imaging times.

Figure 10:
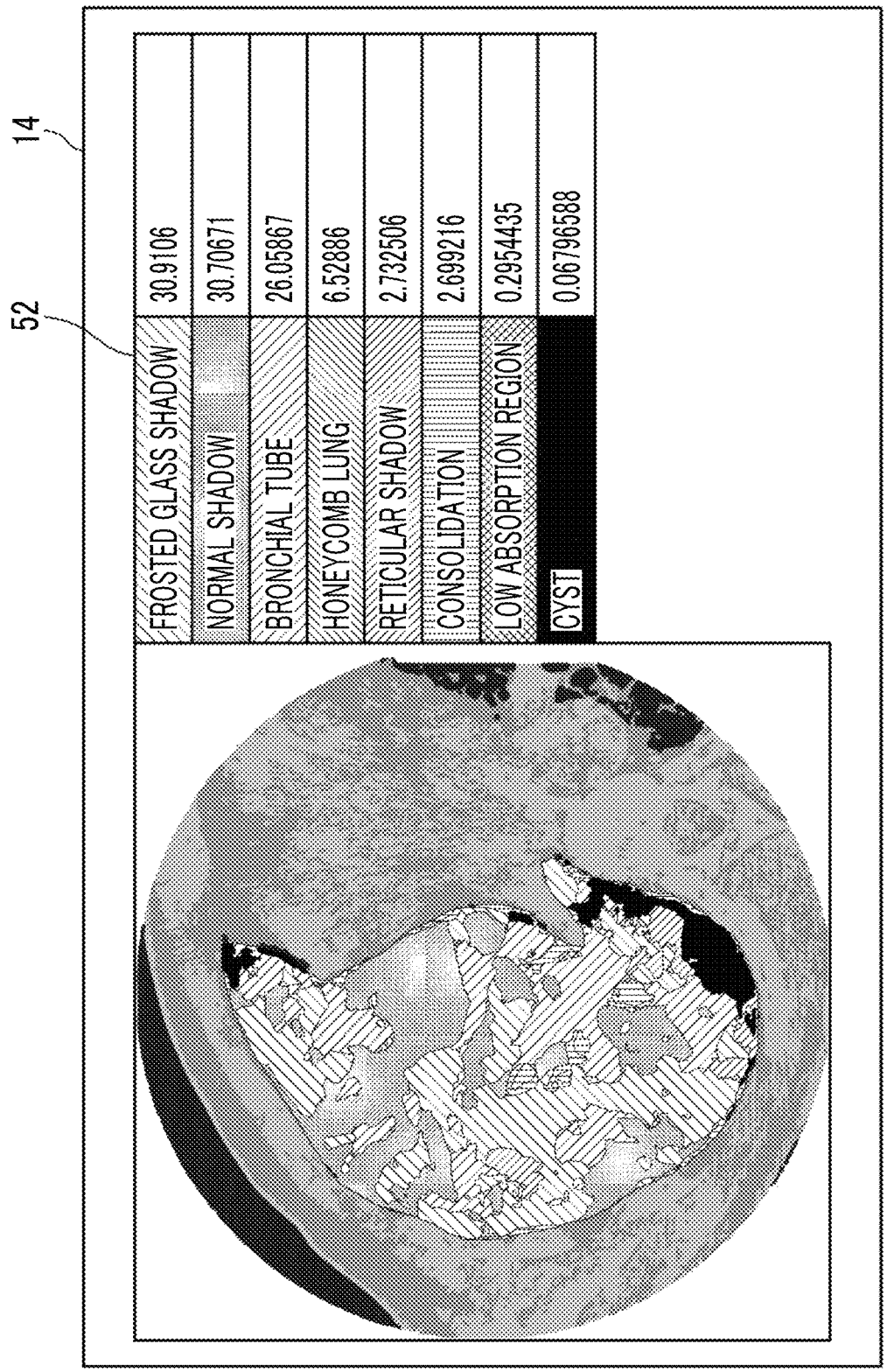
FIG. 10 is a diagram showing information regarding changes displayed in a case where only the amount of change in area is calculated.

In the embodiment described above, the movement amount and the movement direction of the center-of-gravity position of the corresponding case region and the amount of change in the size of the corresponding case region are calculated as changes. However, only the movement amount and the movement direction of the center-of-gravity position of the corresponding case region may be calculated as changes. Alternatively, only the amount of change in the size of the corresponding case region may be calculated as a change. FIG. 10 is a diagram showing information regarding displayed changes in a case where only the amount of change in area is calculated as the amount of change in size. As shown in FIG. 10, the same mapping image M0 as in FIG. 4 and a table 52 showing the amount of change in area are displayed on the display 14. In the table 52, the rate of change is shown as the amount of change in area. In addition, in the table 52, the amount of change is calculated for each of the eight types of case regions.

In the embodiment described above, the three-dimensional images V0 and V1 are read from the image storage server, and classification processing and mapping image generation processing are performed on both the three-dimensional images V0 and V1. However, for the past three-dimensional image, the classification result and the mapping image may be stored together in the image storage server 3, so that the classification result and the mapping image are read together in the case of reading the past three-dimensional image. As a result, since there is no need to perform the classification processing and the mapping image generation processing on past three-dimensional images, the processing can be performed quickly.

In the embodiment described above, information regarding the change of each case region for a plurality of subjects may be stored in the storage 13 or the image storage server 3. In this case, the display control unit 26 may acquire information regarding the change of each case region for a subject different from the subject to be displayed, and the acquired information regarding the change may be further displayed. Therefore, it is possible to predict how each case region included in the subject changes in the future based on the acquired information regarding the change.

Hereinafter, the effect of the present embodiment will be described.

By performing registration between a plurality of medical images and performing registration between a plurality of mapping images based on the registration result, it is possible to more accurately calculate the change of each case region. Therefore, it is possible to more accurately perform the comparative observation over time using a plurality of medical images having different imaging times.

By storing information regarding the change of each case region for a plurality of subjects and acquiring information regarding the change of each case region for a subject different from the subject to be displayed and further displaying the acquired information regarding the change, it is possible to predict how the case region of the subject changes in the future based on the acquired information regarding the change.

What is claimed is:

1. A medical image display device, comprising:
processing circuitry configured to:
classify a target region, which is included in each of a plurality of medical images having different imaging times for the same subject, into a plurality of types of case regions;
generate a mapping image relevant to each of the case regions, which corresponds to each of the plurality of medical images, by labeling each of the case regions;
calculate a center-of-gravity position of a case region at each corresponding position for case regions at corresponding positions in the plurality of mapping images and calculate at least one of a movement amount change or a movement direction change of the center-of-gravity position between the plurality of mapping images as a change of each of the classified case regions between the plurality of mapping images; and
display information regarding the change on a display.

2. The medical image display device according to claim 1, wherein the processing circuitry is further configured to calculate, as the change, an amount of change in a size of a case region at a corresponding position in each of the plurality of mapping images.

3. A medical image display device, comprising:
processing circuitry configured to:
classify a target region, which is included in each of a plurality of medical images having different imaging times for the same subject, into a plurality of types of case regions;
generate a plurality of mapping images corresponding to the plurality of medical images by labeling each of the case regions;
calculate an amount of change in a size of a case region at each corresponding position in each of the plurality of mapping images as a change of each of the classified case regions between the plurality of mapping images; and
display information regarding the change on a display.

4. The medical image display device according to claim 1, wherein the processing circuitry is further configured to:
perform registration between the plurality of medical images and perform registration between the plurality of mapping images based on the registration result.

5. The medical image display device according to claim 4, wherein the processing circuitry is further configured to perform designated registration among first registration for aligning a position of a medical image other than a medical image having an oldest imaging time, among the plurality of medical images, with the oldest medical image, second registration for aligning a position of a medical image other than a medical image having a latest imaging time with the latest medical image, and third registration for aligning a position of a medical image other than a designated medical image with the designated medical image.

6. The medical image display device according to claim 1, wherein the processing circuitry has a discriminator that is deep-learned so as to classify the plurality of types of cases, and classifies the target region into a plurality of types of case regions using the discriminator.

7. The medical image display device according to claim 1, further comprising:
storage for storing information regarding a change of each of the case regions for a plurality of subjects,
wherein the processing circuitry is further configured to acquire information regarding a change of each of the case regions for a subject different from a subject to be displayed from the storage, and further display the acquired information regarding the change.

8. The medical image display device according to claim 3, wherein the processing circuitry is further configured to:
perform registration between the plurality of medical images and perform registration between the plurality of mapping images based on the registration result.

9. The medical image display device according to claim 8, wherein the processing circuitry is further configured to perform designated registration among first registration for aligning a position of a medical image other than a medical image having an oldest imaging time, among the plurality of medical images, with the oldest medical image, second registration for aligning a position of a medical image other than a medical image having a latest imaging time with the latest medical image, and third registration for aligning a position of a medical image other than a designated medical image with the designated medical image.

10. The medical image display device according to claim 3
wherein the processing circuitry has a discriminator that is deep-learned so as to classify the plurality of types of cases, and classifies the target region into a plurality of types of case regions using the discriminator.

11. The medical image display device according to claim 3, further comprising:
storage for storing information regarding a change of each of the case regions for a plurality of subjects,
wherein the processing circuitry is further configured to acquire information regarding a change of each of the case regions for a subject different from a subject to be displayed from the storage, and further display the acquired information regarding the change.

12. A medical image display method, comprising:
classifying a target region, which is included in each of a plurality of medical images having different imaging times for the same subject, into a plurality of types of case regions;
generating a mapping image relevant to each of the case regions, which corresponds to each of the plurality of medical images, by labeling each of the case regions;
calculating a center-of-gravity position of a case region at each corresponding position for case regions at corresponding positions in the plurality of mapping images and calculating at least one of a movement amount change or a movement direction change of the center-of-gravity position between the plurality of mapping images as a change of each of the classified case regions between the plurality of mapping images; and
displaying information regarding the change on a display.

13. A medical image display method, comprising:
classifying a target region, which is included in each of a plurality of medical images having different imaging times for the same subject, into a plurality of types of case regions;
generating a plurality of mapping images corresponding to the plurality of medical images by labeling each of the case regions;
calculating an amount of change in a size of a case region at each corresponding position in each of the plurality of mapping images as a change of each of the classified case regions between the plurality of mapping images; and
displaying information regarding the change on a display.

14. A non-transitory computer-readable storage medium that stores a medical image display program causing a computer to execute:
a step of classifying a target region, which is included in each of a plurality of medical images having different imaging times for the same subject, into a plurality of types of case regions;
a step of generating a mapping image relevant to each of the case regions, which corresponds to each of the plurality of medical images, by labeling each of the case regions;
a step of calculating a center-of-gravity position of a case region at each corresponding position for case regions at corresponding positions in the plurality of mapping images and calculating at least one of a movement amount change or a movement direction change of the center-of-gravity position between the plurality of mapping images as a change of each of the classified case regions between the plurality of mapping images; and
a step of displaying information regarding the change on a display.

15. A non-transitory computer-readable storage medium that stores a medical image display program causing a computer to execute:
a step of classifying a target region, which is included in each of a plurality of medical images having different imaging times for the same subject, into a plurality of types of case regions;
a step of generating a plurality of mapping images corresponding to the plurality of medical images by labeling each of the case regions;
a step of calculating an amount of change in a size of a case region at each corresponding position in each of the plurality of mapping images as a change of each of the classified case regions between the plurality of mapping images; and
a step of displaying information regarding the change on a display.

* * * * *